(12) United States Patent
Lally et al.

(10) Patent No.: US 6,476,192 B1
(45) Date of Patent: Nov. 5, 2002

(54) RECOMBINANT ANTIGENS USEFUL FOR THE SERODIAGNOSIS OF NEOSPOROSIS

(76) Inventors: Nicola C. Lally, 1539 Lincoln Way, Apt. 304, McLean, VA (US) 22102; Mark C. Jenkins, 15715 Pointer Ridge Dr., Bowie, MD (US) 20716; Jitender P. Dubey, 234 Lastner La., Greenbelt, MD (US) 20770

(*) Notice: Subject to any disclaimer, the term of this patent is extended or adjusted under 35 U.S.C. 154(b) by 0 days.

(21) Appl. No.: 08/624,677

(22) Filed: Apr. 15, 1996

(51) Int. Cl.[7] .......................... C07K 1/00; C07K 14/00; C07K 2/00; G01N 33/53
(52) U.S. Cl. ................ 530/350; 30/300; 424/184.1; 424/265.1; 424/266.1; 424/269.1; 435/7.1; 435/7.21; 435/7.92; 435/8; 435/35; 436/538
(58) Field of Search ................ 424/184.1, 265.1, 424/266.1, 269.1; 435/7.1, 7.92, 8, 35, 7.21; 436/538; 530/300, 350

(56) References Cited

U.S. PATENT DOCUMENTS 5,707,617 A * 1/1998 Conrad et al.
5,889,166 A * 3/1999 Conrad et al. ............. 536/23.1
6,376,196 B1 * 4/2002 Conrad et al.

FOREIGN PATENT DOCUMENTS

WO   9739009   * 10/1997

OTHER PUBLICATIONS

Lally et al, Mal. & Biochem. Parasitol 87:239–243, 1997.*
Lally et al. Clin. & Diag. Lab. Immunol 3/3: 275–279, May 1996.*
Liddell et al Mal & Biochem. Parasitol 93:153–158, 1998.*
Bjorkman et al., *Parasite Immunology*, vol. 16, pp. 643–648 (1994).
Bjerkas et al., *Clin. Diagn. Lab. Immunol.*, vol. 1(2), pp. 214–221 (1994).
Conrad et al., *J. Vet. Diagn. Invest.*, vol. 5, pp. 572–578 (1993).
Pare et al., *J. Vet. Diagn. Invest*, vol. 7, pp. 352–359 (1995).

* cited by examiner

Primary Examiner—Nita Minnifield
(74) Attorney, Agent, or Firm—M. Howard Silverstein; John D. Fado; Janelle S. Graeter

(57) ABSTRACT

Antigens for the detection of antibodies to Neospora parasites for the diagnosis of neosporosis have been identified. Recombinant antigens may be produced by expression of DNA sequences derived from *Neospora caninum*. Both antigens are capable of detecting antibody responses in animals experimentally inoculated with *N. caninum* but show no evidence of cross-reactivity with serum from animals inoculated with closely related parasites such as *Toxoplasma gondii* or Sarcocystis species.

8 Claims, 7 Drawing Sheets

SEQ ID NO: 1

Nc4.1 DNA SEQUENCE AND TRANSLATION OF OPEN READING FRAME.

```
  1 gattcggcacgaggcgggcctgccgaggctcgctagcgctggagacttggcaaccgaaca
    I  R  H  E  A  G  L  P  R  L  A  S  A  G  D  L  A  T  E  Q
 61 gcatgaaggggacatcggatatggggttagggcatatgccggcgtttcaaactatgacgg
    H  E  G  D  I  G  Y  G  V  R  A  Y  A  G  V  S  N  Y  D  G
121 cgatgacgatgctgcaggaaaccctgtcgactcggatgtgactgacgatgccattacaga
    D  D  D  A  A  G  N  P  V  D  S  D  V  T  D  D  A  I  T  D
181 tggtgagtggccacgtgttgtatcggggcagaagccgcacacgactcagaaaggcagctt
    G  E  W  P  R  V  V  S  G  Q  K  P  H  T  T  Q  K  G  S  L
241 gatcaagaagctggcagtaccggtggtcggcgctcttacgtcgtatcttgttgctgacag
    I  K  K  L  A  V  P  V  V  G  A  L  T  S  Y  L  V  A  D  R
301 ggtgctgcccgagttgacttctgcagaagaagaaggaacagagtccatccccggtaaaaa
    V  L  P  E  L  T  S  A  E  E  E  G  T  E  S  I  P  G  K  K
361 acgtgtcaagactgccgtgggcatagccgcgttagttgcagcagccgcatttgctggatt
    R  V  K  T  A  V  G  I  A  A  L  V  A  A  A  F  A  G  L
421 gggtctcgcgagaacattcaggcatttcgtgccaaaaaagtcaaagacggttgcgagtga
    G  L  A  R  T  F  R  H  F  V  P  K  K  S  K  T  V  A  S  E
481 ggactctgcgctcggaaacagtgaagagcagtatgtggaaggaaccgtgaacgggagcag
    D  S  A  L  G  N  S  E  E  Q  Y  V  E  G  T  V  N  G  S  S
541 tgatccggaacaggagcgggcgggtgggcctcttatcccggaaggagacgagcaggaagt
    D  P  E  Q  E  R  A  G  G  P  L  I  P  E  G  D  E  Q  E  V
601 agacaccgaatagttatggcaaacagatcgttggcgcagctaacatgtgtttaacatttt
    D  T  E  *
661 tttcgtgtcccagatgacagctgctactgtttgtgtattgttgacagtccacagatgcgt
721 acgtgccgctcccgtgtagaggaaacttttcttttcgcctacctggccgatgagttcc
781 gggatgtgcagtttgtcatagggagctacccccctccaaatggagttctgcgaaccccgt
841 gcatgtgcttgcggatttatgctaattgacagactcgtttctcgatcacgaaaatccgta
901 atttgagaaaaaaaaaaaaaaaaa 925
```

*Fig. 1a*

SEQ ID NO: 3

Nc14.1 DNA sequence and translation of open reading frame.

```
  1  gaattcggcacgagagtatgtcaactcttccgagttagcaggcagtcgtgtgacaaggggaa
        N  S  A  R  E  Y  V  N  S  S  E  L  A  G  S  R  D  K  G  N
 61  cgcggaagcggaagaagccgctgagttgagactgttcagccttccagctgac
        A  E  A  E  E  A  A  E  V  E  T  D  V  Q  P  S  S  V  T
121  gattgatacggaggaacgcgggcaccagtcaggtacagcaagagagaatgga
        I  D  T  E  E  R  A  A  P  S  Q  V  Q  Q  E  R  M  E
181  agaagctgacgatgtcctccgaaacctgttccggtgcggtcggcgtcctacagtggc
        E  A  D  D  A  P  K  P  V  P  V  R  S  A  V  P  S  T  V  A
241  gaaacggcagcaggcacgtcacagagtcattggacagcggtgatagcggcagtagttgc
        K  R  Q  Q  A  R  H  R  V  I  G  T  A  V  I  A  A  V  V  A
301  ggcacttctttgaagtttcgagacgccgcccacgtgagggggaaaa
        A  L  W  K  F  S  R  R  R  S  G  A  P  R  E  G  G  E  N
361  tgaaaacggcgggaggaaaaataggaaacgccggggaccaaatggaaacggcgcggggt
        E  N  G  G  E  E  K  *
421  caactgaccaatatgcgtattgaacaaacagatacacccggagtgtgtaggtgcgagtcg
481  cggggaactctgtgacagtcggcgccgagaaatgctgcgacacagccagaccgtcacaa
541  gcggggaggaacggcaaagtttggagaatgcacttgtgggagagtcggtgcgagacagc
601  tcgag  605
```

FIG. 1b

RECOMBINANT ANTIGENS USEFUL FOR THE SERODIAGNOSIS OF NEOSPOROSIS

BACKGROUND OF THE INVENTION

1. Field of the Invention

Infection by Neospora parasites results in neosporosis, a disease which causes paralysis and death in dogs (Dubey et al. 1988. *J. Am. Vet. Med. Assoc.* vol. 192, pp. 1269–1285) and abortion and neonatal morbidity and mortality in cattle, sheep, goats and horses (Dubey and Lindsay. 1993. *Parasitol. Today.* vol. 9, pp. 452–458). Methods for detection of the parasite are available, however, definitive diagnosis of neosporosis has often been difficult to achieve. This invention relates to recombinant antigens isolated from *Neospora caninum* (*N. caninum*) which have provided an effective means for diagnosing the disease.

2. Description of the Related Art

Diagnosis of abortion due to neosporosis may be achieved by demonstration of the presence of the parasite in tissues of aborted fetuses by immunohistochemical identification (Lindsay and Dubey. 1989. *Am. J. of Vet. Res.* vol. 50, pp. 1981–1983). Few parasites are present, however, and aborted fetuses may be severely autolysed; therefore, recovery of parasites from fetal samples useful for this purpose is often not possible.

An immunofluorescent antibody test (IFA) has been developed for the serodiagnosis of neosporosis using *N. caninum* tachyzoites. The use of whole tachyzoites for immunodiagnosis may result in false positives, however, since there appear to be antigens that are conserved between *N. caninum* tachyzoites and the closely related protozoan *Toxoplasma gondii* (Conrad et al. 1993. *J. Vet. Diagn. Invest.* vol. 5, pp. 572–578; Dubey and Lindsay, supra), therefore some cross-reaction may be expected to occur. Other drawbacks associated with the tachyzoite IFA include the requirement for growing the parasite in vitro, which is time-consuming and expensive, and the need for trained personnel to interpret IFA slides.

A method for the detection of antibodies to *N. caninum* in serum from dogs by indirect enzyme-linked immunosorbent assay (ELISA) has been described (Björkman et al. 1994. *Parasite Immunology.* vol. 16, pp. 643–648). This method utilizes proteins extracted from *N. caninum* tachyzoites as antigens. Similarly, an ELISA for the diagnosis of neosporosis in cattle was developed using sonicated tachyzoites of Neospora isolated from an aborted bovine fetus as antigen (Paré et al. 1995. *J. Vet. Diaan. Invest.* vol. 7, pp. 352–359). These tests are capable of detecting the presence of antibodies to Neospora sp.; however, as with the IFA method, antigens which are conserved between Neospora sp. and other similar protozoa are more than likely present in the antigen preparations, thus the possibility of cross-reaction still exists. The search therefore continued for antigens having increased sensitivity and specificity for use in immunological procedures for the diagnosis of the disease.

SUMMARY OF THE INVENTION

We have discovered antigens derived from *N. caninum* tachyzoites which are highly specific and sensitive for the detection of antibodies present in animals suffering from neosporosis and which are not present in morphologically-related parasites.

In accordance with this discovery, it is an object of the invention to provide novel antigens effective for the detection of antibodies to Neospora and for the serodiagnosis of neosporosis.

It is a further object of the invention to provide DNA sequences which encode antigens effective for the detection of antibodies to Neospora and for the diagnosis of neosporosis.

It is also an object of the invention to provide an immunoassay method effective for detecting antibodies to Neospora present in a sample suspected of containing said antibodies.

Other objects and advantages of the invention will become readily apparent from the following description.

BRIEF DESCRIPTION OF THE DRAWINGS

FIG. 1 shows the DNA sequences of the two clones Nc4.1, SEQ ID NO: 1 (1A) and Nc14.1, SEQ ID NO: 3 (1B).

DETAILED DESCRIPTION OF THE INVENTION

Figure 2:
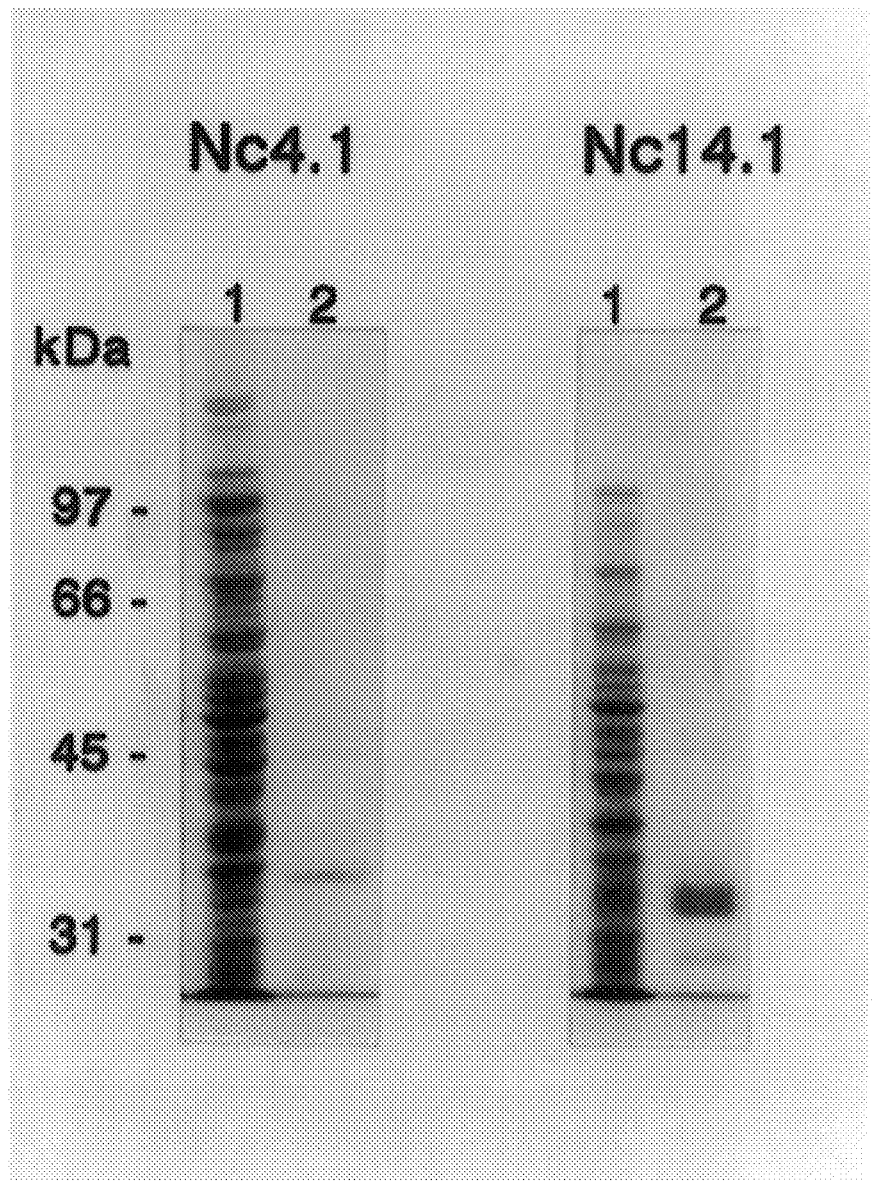
FIG. 2 shows the column purification of recombinant antigens expressed by Nc4.1 and Nc14.1. Lanes 1, lysate prepared from induced culture before purification procedure; lanes 2, purified recombinant antigen eluted from Ni-nitrilotriacetic acid column.

*Neosporum caninum* is a newly-discovered apicomplexan parasite which causes paralysis and death in dogs (Bjerkas et al. 1984. *Z. Parasitenkd.* vol. 70, pp. 271–274; Dubey et al., supra). The detection of Neospora sp. in dogs, goats, sheep and horses is important. Its detection in cattle, however, is critical since neosporosis is emerging as a major cause of abortion in cattle in the United States and in other countries (Anderson et al. 1991. *J. Am. Vet. Med. Assoc.* vol. 198, pp. 241–244). In one study of 14 herds of California dairy cattle, neosporosis was the most frequently identified cause of abortion, being responsible for 42.5% of abortions for which a cause was identified (Anderson et al. 1995. *J. Am. Vet. Med. Assoc.* vol. 207, pp. 1206–1210). In order to more effectively manage the occurrence of the disease among herds of cattle, it is therefore necessary to be capable of distinguishing between aborted fetuses due to neosporosis and those due to other causes.

Investigations were carried out in order to develop a diagnostic assay specific for the disease. Neospora was a newly-discovered organism and not fully characterized, but it was known that there were many similarities, morphologically and immunologically, to other related parasites. The likelihood of discovering antigens which would-serke as effective markers for the disease was therefore uncertain.

Recombination methods were utilized to identify and purify possible useful antigens. A *N. caninum* tachyzoite cDNA library (Lally et al. 1996. *Molecular and Biochemical Parasitology.* In press.) was immunoscreened with serum from a cow experimentally infected with Neospora (Dubey et al. 1992. *J. Am. Vet. Med. Assoc.* vol. 201, pp. 709–713) and with fetal bovine serum (FBS) containing antibodies reactive with *N. caninum* tachyzoites in IFA. Two clones were selected and designated λNc4.1 and λNc14.1. The recombinant antigens were identified and purified utilizing conventional recombinant techniques as described in Examples 1–5. Following the initial screening procedure, the two clones were purified by plaque-purification and subcloned into the plasmid pBluescript (BSNc4.1 and BSNc14.1). Western blots revealed that BSNc4.1 expressed a recombinant protein which was recognized by FBS and by serum from a cow experimentally infected with N. caninum, but not by pre-inoculation serum. BSNc14.1 expressed a protein which was recognized by serum from an experimentally infected cow, but not by pre-inoculation serum. Apparent molecular weights of the two proteins as estimated by Western blotting were approximately 35 kDa (Nc4.1) and approximately 30 kDa (Nc14.1).

Both DNA inserts were sequenced (see FIG. 1). The Nc4.1 insert comprises an approximately 925-bp fragment, and the Nc14.1 insert comprises an approximately 605-bp fragment. Both contain an open reading frame (ORF) starting at nucleotide 2 that is in frame with the i-galactosidase sequence encoded by the pBluescript vector. These ORFs therefore are sequences that, when translated, result in the expression of the above-mentioned recombinant fusion proteins by plasmids BSNc4.1 and BSNc14.1 respectively. Both the DNA sequences and the deduced amino acid sequences were compared with known sequences in available databases. No DNA or protein sequences which were substantially similar to either Nc4.1 or Nc14.1 were identified. For DNA sequences, the highest degree of similarity was 59% identity over a 122-bp region. For protein sequences, the most similar sequences were in the order of 31% identical over a 45-amino acid region. None of these sequences were considered substantially homologous to either Nc4.1 or Nc14.1.

The two clones were deposited in the American Type Culture Collection, 10801 University Blvd., Manassas, Va. 20110–2209 on Mar. 12, 1996 under terms of the Budapest Treaty. Plasmid BSNc14.1 was given the designation ATCC No.98009, and plasmid BSNc4.1 was given the designation ATCC No. 98010. Any restrictions on the deposit will be irrevocably removed upon issuance of a patent.

The invention encompasses DNA sequences encoding the antigens expressed by BSNc4.1 and BSNc14.1 ORFs (as shown in FIG. 1) as well as DNA sequences having substantial homology thereto. Those sequences having substantial homology are those which encode antigens capable of eliciting or detecting antibodies to Neospora or those which are capable of eliciting or detecting antibodies cross-reactive with those against the Nc4.1 or Nc14.1 antigens. Also included are fragments which encode the epitopes capable of binding to said antibodies. The protein sequences encoded by Nc4.1 and Nc14.1 (as shown in FIG. 1) are either expressed from recombinant DNA molecules or are produced synthetically or by isolation from Neospora tachyzoites. In addition, proteins which represent incomplete portions of the ORFs or proteins which are not identical to but are sufficiently similar as to be able to bind to or elicit production of antibodies to Nc4.1 or Nc14.1 antigens or which cross react with those against the Nc4.1 or Nc14.1 antigens are included.

The DNA inserts from BSNc4.1 and BSNc14.1 were subcloned into the expression vector pTrcHisB in order to purify the proteins for use in ELISA. This vector expresses foreign genes as N-terminal fusion proteins with a $His_6$ tag which allows purification using a nickel-chelating affinity resin. Overnight induction of the resulting clones, followed by purification on an affinity column resulted in the recovery of substantial amounts of relatively pure recombinant fusion protein expressed by both Nc4.1 and Nc14.1 (FIG. 2).

Figure 3A:
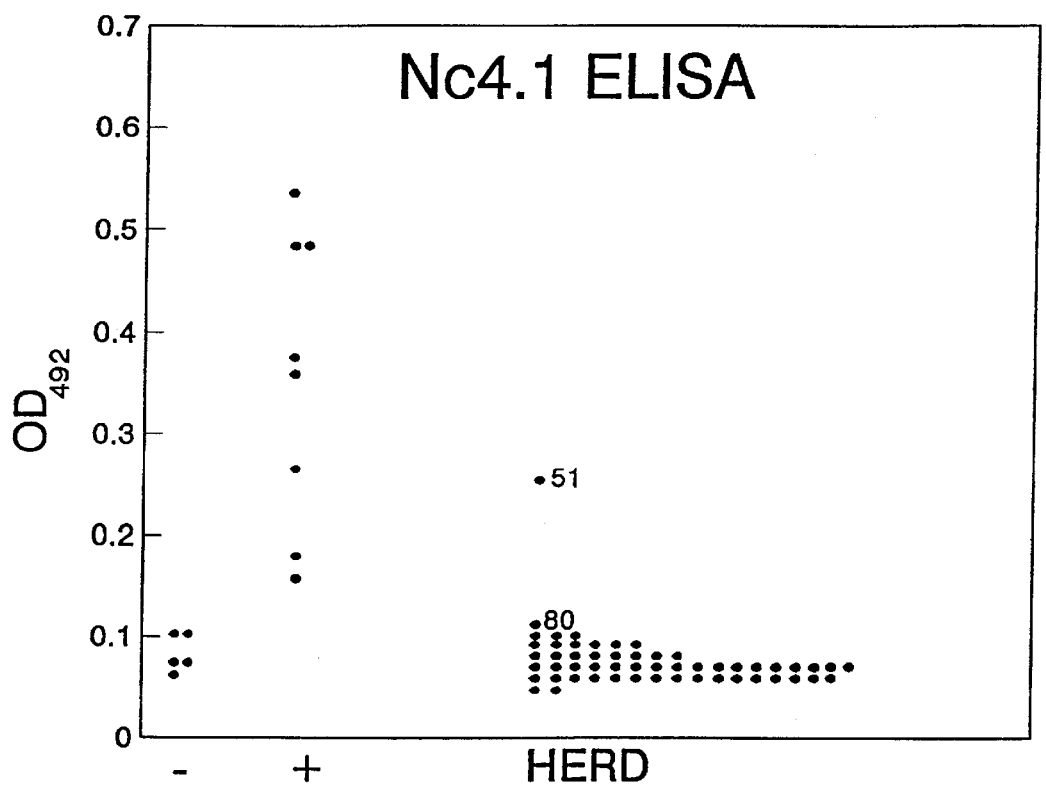
FIG. 3 shows ELISA results for eight cows which aborted Neospora-infected calves (+) and five normal cows from the same herd (−). Sera from a herd of 54 cows were also tested (HERD). Two of these had recently aborted due to neosporosis and were positive by *N. caninum* IFA (#51 and #80). Panel A shows the results using Nc4.1 and panel B using Nc14.1.
Figure 3B:
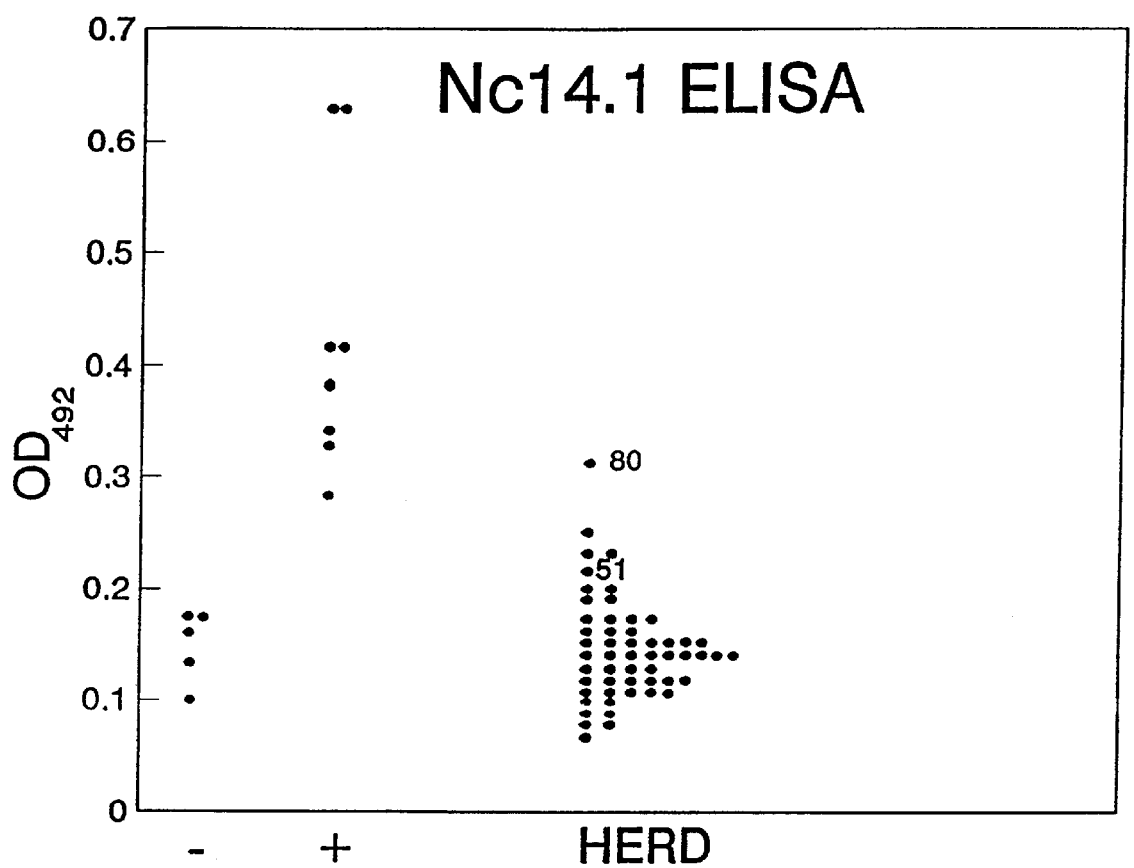

The recombinant antigens were tested in an ELISA utilizing sera from naturally-infected cattle, and results showed that both antigens were able to differentiate between naturally-infected and normal control bovine sera. Sera from 8 cows that had aborted Neospora-infected calves were tested by ELISA using both antigens. All 8 sera were positive by N. caninum tachyzoite IFA. Sera from 5 cattle from the same herd, having no history of abortion and testing negative by N. caninum tachyzoite IFA, were included as normal control. OD values of serum from cows that had aborted Neospora-infected calves were all higher than those from normal controls in both Nc4.1 and Nc14.1 ELISA (FIG. 3).

Serum samples from a herd of 54 cattle were also tested, two of which (#51 and #80) had aborted due to Neospora infection and had high titers by IFA. The remaining sera were negative by IFA. Serum from cow #80 had a high reading by Nc14.1 ELISA (0.31), but the Nc4.1 OD value was intermediate between those of infected and normal controls. Conversely, serum from cow #51 had a high reading by Nc4.1 ELISA, but the Nc14.1 OD reading was intermediate between those of infected and control sera. In addition to these two IFA-positive sera, there were several animals in this herd that had OD readings in Nc14.1 ELISA that were intermediate between values for infected and normal controls (FIG. 3). The two recombinant antigen ELISAs appear to complement one another in being able to identify animals that are positive by IFA. Sera that were intermediate between values for infected and control animals by ELISA may represent infected animals that were not detected due to insufficient sensitivity of the IFA.

Figure 4A:
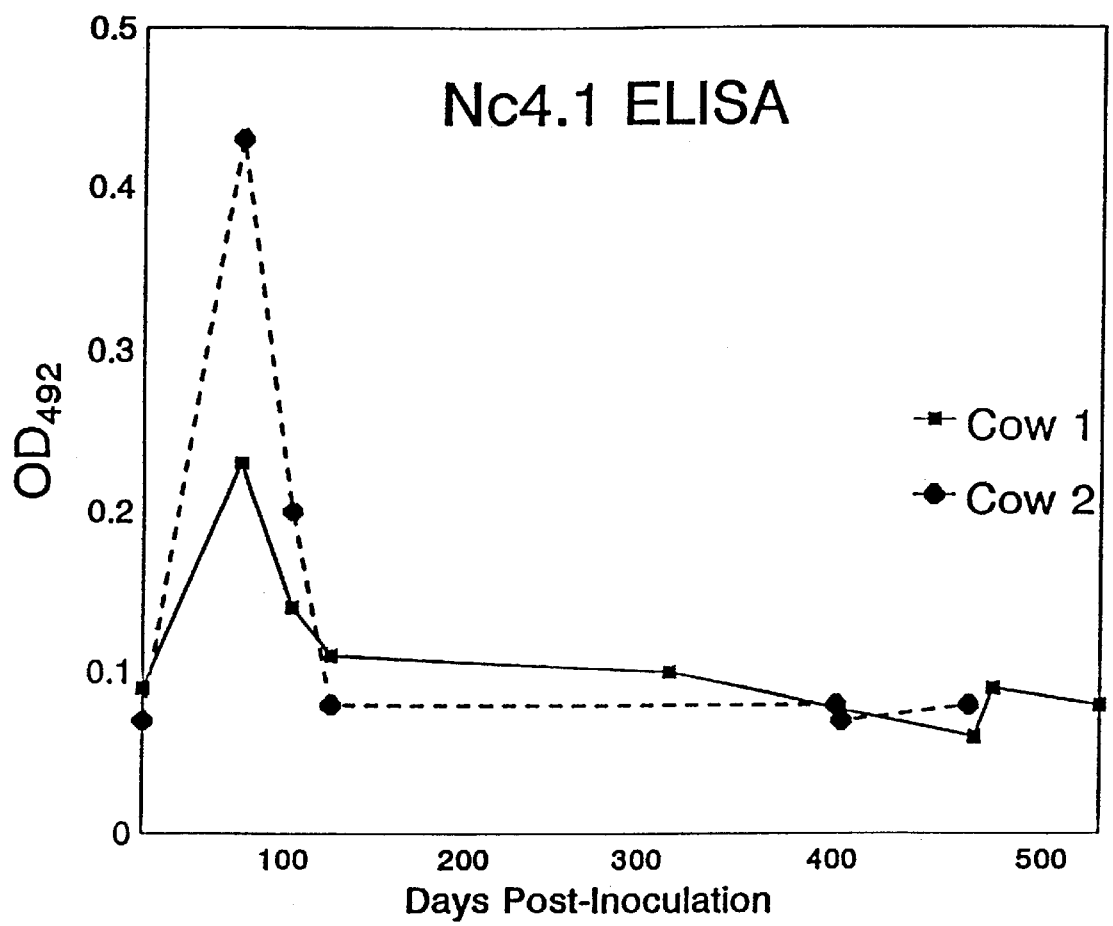
FIG. 4 shows ELISA results for two cows that were experimentally inoculated with *N. caninum*. Panel A shows the results using Nc4.1 and panel B using Nc14.1.
Figure 4B:
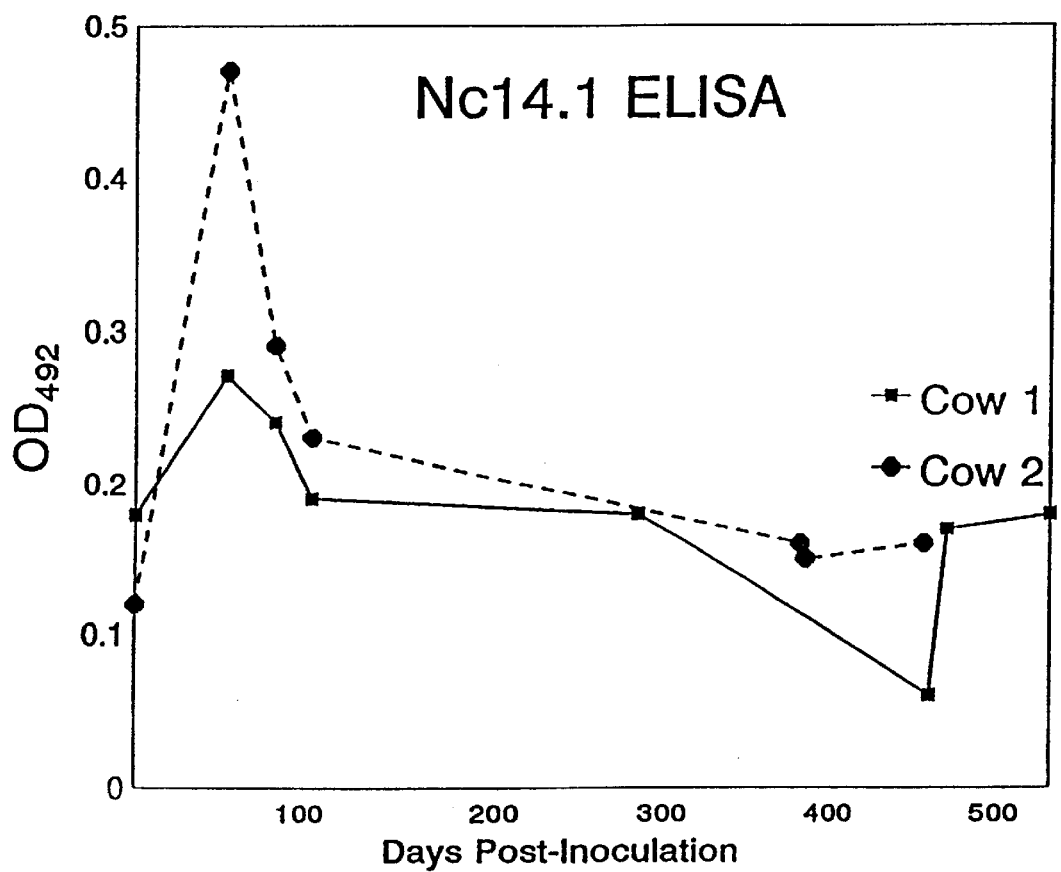

ELISA results on sera from two experimentally-inoculated cows (FIG. 4 and Table 1) showed that IFA titers remained elevated for a longer period of time than did antibody levels as measured by recombinant ELISA, suggesting that IFA may be more sensitive than either Nc4.1 or Nc14.1 ELISA for the detection of antibodies to Neospora in experimentally inoculated animals. Both animals had elevated levels of antibody both as measured by Nc4.1 and Nc14.1 54 days post-inoculation (DPI). However, antibody levels had returned almost to prebleed levels in both animals by 103 DPI in contrast to levels measured by IFA, which remained elevated for at least 400 DPI (Table 1). These differences may be attributable to differences between antibody responses to experimental inoculation and to natural infections.

TABLE 1

|  | Cow 1 | | | Cow 2 | | |
| --- | --- | --- | --- | --- | --- | --- |
| DPI | IFA | Nc4.1 ELISA | Nc14.1 ELISA | IFA | Nc4.1 ELISA | Nc14.1 ELISA |
| 0 | <50 | 0.09 | 0.18 | 50 | 0.07 | 0.12 |
| 54 | 1600 | 0.23 | 0.27 | 6400 | 0.43 | 0.47 |
| 82 | 1600 | 0.14 | 0.24 | 3200 | 0.20 | 0.29 |
| 103 | 400 | 0.11 | 0.19 | 1600 | 0.08 | 0.23 |
| 284 | 200 | 0.10 | 0.18 | ND | ND | ND |
| 375 | ND | ND | ND | 800 | 0.08 | 0.16 |
| 378 | ND | ND | ND | 800 | 0.07 | 0.15 |
| 446 | ND | ND | ND | 400 | 0.08 | 0.16 |
| 449 | 800 | 0.06 | 0.06 | ND | ND | ND |
| 459 | 200 | 0.09 | 0.17 | ND | ND | ND |
| 516 | 400 | 0.08 | 0.18 | ND | ND | ND |

Serum from three 4–6 week-old calves experimentally inoculated with N. caninum and one uninoculated control calf was drawn over time, and samples were tested by Nc4.1 and Nc14.1 ELISA and IFA (Table 2). Calf 508 (control) had antibody levels which remained low throughout the experiment, as measured by all three assays. Calf 510 (inoculated IM) appeared to have been previously exposed to Neospora on the basis of IFA titers and reactivity to Nc4.1; however, an elevated antibody titer to Nc14.1 was only detected on day 42 post-infection. Calf 509 (inoculated SC) exhibited elevated antibody levels as measured by all three assays from 21 to 46 DPI. Calf 511 (inoculated IV) had high antibody levels as measured by all three assays from 21 to 46 DPI. An antibody response to Nc14.1 developed slightly earlier in this animal, i.e. at 14 DPI. Results from the experimentally inoculated calves showed a noticeable correlation between IFA and both ELISAs (Table 2).

The specificity of Nc4.1 and Nc14.1 ELISAs with respect to closely-related apicomplexan parasites was investigated using Immunoassay methods are well-known in the art, and, although ELISA was the preferred method in the studies described herein, any effective assay method is useful with the recombinant antigens. Essentially, antigen is combined with a sample suspected of containing antibody reactive with the antigen to form a reaction mixture, the reaction mixture is incubated for a time sufficient to allow binding between antigen and antibody to occur, bound antigen-antibody complex is separated from any unbound immunoreagents present in the sample, and bound complex is detected by means of an effective label. The binding step may be direct or indirect, competitive or non-competitive. The separation step may be carried out by precipitating the immunocomplex and washing to remove unreacted reagents or, alternatively, where antigen has been adsorbed to a solid phase, by washing the solid phase having bound immunocomplex attached. Effective means for detection include a

TABLE 2

|  | 508 | | | 509 | | | 510 | | | 511 | | |
| --- | --- | --- | --- | --- | --- | --- | --- | --- | --- | --- | --- | --- |
| DPI | IFA | Nc4.1 ELISA | Nc14.1 ELISA | IFA | Nc4.1 ELISA | Nc14.1 ELISA | IFA | Nc4.1 ELISA | Nc14.1 ELISA | IFA | Nc4.1 ELISA | Nc14.1 ELISA |
| 0 | <50 | 0.07 | 0.07 | <50 | 0.12 | 0.10 | 1600 | 0.45 | 0.20 | <50 | 0.06 | 0.23 |
| 7 | <50 | 0.08 | 0.20 | <50 | 0.07 | 0.09 | 1600 | 0.39 | 0.19 | <50 | 0.05 | 0.07 |
| 14 | <50 | 0.09 | 0.07 | <50 | 0.14 | 0.19 | 1600 | 0.39 | 0.20 | <50 | 0.10 | 0.34 |
| 21 | <50 | 0.08 | 0.09 | 200 | 0.40 | 0.46 | 1600 | 0.40 | 0.22 | 400 | 0.48 | 0.53 |
| 28 | <50 | 0.08 | 0.11 | 800 | 0.46 | 0.43 | 1600 | 0.35 | 0.22 | 6400 | 0.47 | 0.75 |
| 35 | <50 | 0.08 | 0.13 | 3200 | 0.49 | 0.52 | 1600 | 0.27 | 0.17 | 3200 | 0.48 | 0.78 |
| 42 | <50 | 0.09 | 0.15 | 1600 | 0.46 | 0.46 | 1600 | 0.48 | 0.48 | 6400 | 0.48 | 0.79 |
| 46 | <50 | 0.09 | 9.13 | 1600 | 0.44 | 0.38 | 1600 | 0.24 | 0.14 | 12800 | 0.47 | 0.78 | serum from animals that were experimentally inoculated with *T. gondii* or Sarcocystis species. Ten cattle were orally inoculated with *T. gondii* oocysts, and 13 cattle were orally inoculated with Sarcocystis sporocysts. ELISA OD values for these sera were all within the range of the normal control sera (OD≦0.07 for Nc4.1 and ≦0.13 for Nc14.1), with the exception of samples from two animals. Both of these animals had higher pre-inoculation than post-inoculation OD values, suggesting that reactivity to Nc4.1 and Nc14.1 was not due to inoculation with *T. gondii* or Sarcocystis species, but was likely to be a result of natural infection with Neospora.

An important factor to consider when interpreting the data described above concerns the status of the normal control sera used to evaluate the ELISA assays. These sera were from animals that were presumed to be uninfected with Neospora on the basis of non-reactivity in the *N. caninum* tachyzoite IFA and no history of abortion. However, it is known that congenital infection of calves can occur, and in some cases such calves appear clinically normal (Barr et al. 1993. *J. Am. Vet. Med. Assoc.* vol. 202, pp. 113–117). It was therefore impossible to guarantee that a particular animal had not been previously exposed to Neospora. Another factor to consider is the possible effect of route of infection on serological responses to neosporosis. The complete life cycle of Neospora is unknown, and currently the only known route of infection is congenital infection. It is believed, however, that Neospora oocysts are passed in the feces of an unidentified definitive host, and cattle may be infected by ingestion of oocysts. It is possible that the course of infection and nature of the immune response may be dependent on the route of infection, which may partly explain the differences between naturally and experimentally infected cattle in their antibody responses as measured by IFA and ELISA.

wide variety of labels such as radioactive, enzymatic, fluorescent, luminescent or chemiluminescent. The ELISA method is the preferred embodiment.

The following examples are intended only to further illustrate the invention and are not intended to limit the scope of the invention as defined by the claims.

EXAMPLES

Example 1

Identification of Immunoreactive *N. caninum* Tachyzoite CDNA Clones.

A CDNA library of *N. caninum* was prepared by culturing *N. caninum* tachyzoites in vitro in Hs68 cells as described by Dubey et al. (1996. *American Journal of Veterinary Research.* vol. 57, pp. 329–336). Tachyzoites were harvested by removing the medium and replacing with sterile Hanks' balanced salt solution (HBSS), then scraping the monolayer vigorously to release intracellular tachyzoites. The suspension was then expressed through a 27 gauge needle and filtered through a sterile 3 mm polycarbonate filter (Nucleopore Corp., Pleasanton, Calif.). Total *N. caninum* MRNA was prepared by resuspending parasites in a mixture of guanidinium thiocyanate, sodium citrate, phenol and sodium acetate followed by centrifugation and ethanol precipitation using standard procedures as described by Xie and Rothblum (1991. *Biotechniques.* vol. 11, pp. 324–327). Poly A(+) RNA was isolated by passing total *N. caninum* WRNA through an oligo dT spun column. cDNA was prepared by reverse transcription of the mRNA using a primer with a poly-T sequence joined to an XhoI site, followed by second strand synthesis using T4 DNA polymerase. Newly synthesized CDNA was fractionated by gel filtration through a Sepharose CL4B column (Pharmacia/LKB, Piscataway, N.J.) in order to select cDNA greater than 250 bp. EcoRI adaptors were ligated to the blunt ends of cDNA molecules, then the cDNA ligated into the bacteriophage expression vector UNIZAP XR. The unamplified cDNA library consisted of $3\times10^6$ plaque forming units (pfu) and greater that 95% recombinants as indicated by plating on media containing a chromogenic substrate (5-bromo-4-chloro-3-indolyl phosphate). Following amplification on *Escherichia coli* (*E. coli*) XL 1-Blue the library contained $8\times10^9$ pfu and greater than 95% recombinants.

Serum used for immunoscreening was prepared by inoculating a Jersey cow with a pool of three isolates [NC-1 (Dubey et al. 1988. *J. Am. Vet. Med. Assoc.* vol. 193, pp. 1259–1263), NC-2 (Hay et al. 1990. *J. Am. Vet. Med. Assoc.* vol. 197, pp. 87–89) and NC-3 (Lindsay et al. 1991. *J. of the Alabama Academy of Science*. vol. 62, pp. 1–8)] of *N. caninum* containing tachyzoites and tissue cysts 81 days after breeding (Dubey et al., 1992, supra). Serum taken from the cow 3 months after inoculation was used for screening the *N. caninum* CDNA library. Fetal bovine serum was obtained from Sigma Chemical Co. (St. Louis, Mo.) and tested for antibodies against *N. caninum* using the *N. caninum* IFA test (Dubey et al. 1996. *Am. J. Vet. Res.* vol. 57, pp. 329–336).

The amplified cDNA library was plated on *E. coli* XL 1-Blue and immunoscreened by standard procedures (as described by Huynh et al. 1985. In *DNA Cloning*, D. M. Glover, ed. vol. I, pp. 49–78, IRL Press, Oxford, UK) using serum from an experimentally *N. caninum*-infected cow and FBS which had previously been shown to contain antibodies against *N. caninum*. Immunoreactive clones λNc14.1 and XNc4.1 were identified with the infected cow serum and FBS, respectively. Both clones were purified by repeated rounds of screening and single plaque isolation.

Example 2

Preparation of Subcloned in pBluescript

Recombinant pBluescript plasmid clones were prepared from λNc4.1 and λNc14.1, designated BSNc4.1 and BSNc14.1, respectively, by using an in vivo excision protocol supplied by the manufacturer (Stratagene). Plasmid DNA was sequenced using, the dideoxy-chain termination method, and reagents and protocols from U.S. Biochemical (Cleveland, Ohio). The amino acid sequences of the immunoreactive protein expressed by clones Nc4.1 and Nc14.1 were deduced based on the reading frame of the β-galactosidase fusion protein in pBluescript and the DNA sequences of the inserts. The Nc4.1 insert was 925 bp in length with a poly-A tail at the 3' end, and an ORF extending from bp 2 to 610. The Nc14.1 insert was 605 bp with an ORF extending from bp 2 to 382.

Example 3

SDS-PAGE and Western Blotting

SDS-PAGE was carried out using 10% acrylamide gels according to the method of Laemmli (1970. *Nature,* vol. 227, pp. 680–685). Proteins were electrophoretically transferred to PVDF membranes (Millipore Corp., Bedford, Mass.) using the method of Towbin et al. (1979. *Proc. Natl. Acad. Sci. USA*. vol. 76, pp. 4350–4354). Membranes were blocked for 30 min in 1% bovine serum albumin (BSA), washed once in PBST (PBS containing 0.5% Tween-20) then incubated with primary antibody at 4° C. overnight. After washing three times with PBST, membranes were incubated with biotinylated anti-bovine IgG antisera (Kirkegaarde and Perry Laboratories, Inc., Gaithersburg, Md.), followed by, avidin-peroxidase conjugate (Sigma Chemical Co., St. Louis, Mo.). Immunoreactive proteins were detected using peroxidase substrate [0.06%(w/v) 4-chloro-1-naphthol and 0.02% hydrogen peroxide in PBS].

Example 4

DNA Sequencing

Di-deoxy chain termination DNA sequencing (Sanger et al. 1977. *Proc. Natl. Acad. Sci. USA*. vol. 74, pp. 5463–5467) was carried out using a DNA sequencing kit (USB, Cleveland, Ohio) and recombinant pBluescript plasmid DNA as template. M13 universal and reverse primers, and several custom primers complementary to Nc4.1 and Nc14.1 sequences were used. DNA and protein sequence database searching was carried out using the FASTA program of the GCG sequence analysis software package (Devereaux. 1984. *Nucleic Acids Res*. vol. 12, pp. 387–395).

Example 5

Preparation of Subclones in pTrcHisB and Purification of Proteins

In order to express the recombinant proteins in a form in which they could be more easily purified, both inserts were subcloned in the expression vector pTrcHisB (Invitrogen, San Diego, Calif.). This plasmid vector expresses foreign proteins as fusion proteins with a $His_6$ tag, allowing purification using a nickel chelating affinity column. Both inserts were excised from pBluescript by digestion with BamHI and KpnI, then ligated into similarly digested pTrcHisB plasmid DNA.

For expression of the recombinant fusion proteins, pTrcHisB clones were grown overnight in *E. coli* at 37° C. with 1 mM isopropyl-β-D-thiogalactopyranoside. Cells from 50-ml cultures were centrifuged at 3000×g for 10 min, then resuspended in 10 ml 0.5M NaCl, 20 mM sodium phosphate, pH 7.8. Phenylmethylsulphonyl fluoride (PMSF) and lysozyme were added to final concentrations of 1 mM and 100 μg/ml, respectively, and the mixture was left on ice for 15 min before being sonicated for three 10-sec bursts on setting 8 of a Microson ultrasonic cell disrupter (Heat Systems, Inc., Farmingdale, N.Y.). The lysate was then frozen at −70° C. After thawing at 37° C., the sonication-freeze-thaw cycle was repeated two additional times, and the lysate was centrifuged at 3,000×g for 15 min.

The supernatant was discarded, and the pellet was dissolved in 6 ml of 6M guanidine-HCl, 0.5 M NaCl, 20 mM sodium phosphate, pH 7.8. The resulting solution was mixed with 2 ml Ni-nitriloacetic acid resin (Qiagen, Chatsworth, Calif.) that had previously been equilibrated with binding buffer (8 M urea, 0.5 M NaCl, 20 mM sodium phosphate, pH 7.8). Binding was carried out for 20 min at room temperature. The resin was drained and washed with binding buffer until the ODD of the eluate was <0.01. Further washing was carried out with 8 M urea, 0.5 M NaCl, 20 mM sodium phosphate, pH 6.0. The fusion protein was eluted by applying 8M urea, 0.5 M NaCl, 20 mM sodium phosphate, pH 4.0, and 0.5 ml fractions were collected. An aliquot of 5 μl from each fraction was electrophoresed through a 10% acrylamide gel and stained with Coomassie blue to determine which contained the fusion protein. The concentration of protein was estimated using the BCA protein assay (Pierce, Rockford, Ill.).

Example 6

ELISA Method

Purified recombinant antigen (Nc4.1 or Nc 14.1) was diluted to 0.5 μg/ml in 0.04 M $Na_2CO_3$, 0.06 M $NaHCO_3$, pH 9.5. ELISA 96-well plates (Costar, Cambridge, Mass.) were coated with 100 μl of diluted antigen per well for 1 hr at 37° C. All subsequent incubations were carried out at room temperature. Non-specific binding was blocked by incubating wells with 100 μl of 5% non-fat dried milk diluted in PBS for 1 hr. Plates were washed once with PBST, then incubated with 100 μl of serum diluted 1:400 (Nc4.1) or 1:200 (Nc14.1) in PBST for 1 hr. Plates were washed three times with PBST, then incubated with 100 μl goat anti-bovine IgG heavy and light chain specific horseradish peroxidase conjugate (Kirkegaarde and Perry Laboratories, Inc., Gaithersburg, Md.) for 1 hr. After washing three times with PBST, 50 μl of substrate solution (0.1 mg/ml 0-phenylene diamine, 0.01% $H_2O_2$) was added to each well. After 15 min the reaction was stopped by the addition of 50 μl of 2%(v/v) $H_2SO_4$. ELISA plates were read at absorbance 492 nm.

All references cited hereinabove are herein incorporated by reference.

---

We claim:

1. An isolated and purified antigenic protein which specifically detects antibodies to Neospora, said protein comprising an approximately 35-kDa protein which is immunologically reactive with antibodies to Neospora and comprises the amino acid sequence of SEQ ID NO: 2 or a sequence having substantial homology thereto, or a portion of said protein which is immunologically reactive with antibodies to Neospora and comprises a fragment of SEQ ID NO: 2 or a sequence having substantial homology thereto, said fragment having at least one epitope which binds to said antibodies.

2. An isolated and purified antigenic protein which specifically detects antibodies to Neospora, said protein comprising an approximately 30-kDa protein which is immunologically reactive with antibodies to Neospora and comprises the amino acid sequence of SEQ ID NO: 4 or a sequence having substantial homology thereto, or a portion of said protein which is immunologically reactive with antibodies to Neospora and comprises a fragment of SEQ ID NO: 4 or a sequence having substantial homology thereto, said fragment having at least one epitope which binds to said antibodies.

3. A composition comprising a mixture of said antigenic protein of claim 1 and said antigenic protein of claim 2.

4. An immunoreagent effective for the detection of antibodies to Neospora and the diagnosis of neosporosis, said immunoreagent comprising antigenic protein selected from the group consisting of said antigenic protein of claim 1, said antigenic protein of claim 2, and a mixture of said antigenic protein of claim 1 and said antigenic protein of claim 2, and a diluent.

5. A method of detecting antibodies to Neospora and diagnosing neosporosis, said method comprising a) combining a sample suspected of containing said antibodies with antigenic-protein which specifically detects said antibodies to form a reaction mixture, b) allowing said mixture to incubate for a time sufficient for binding between said antibodies and said antigenic protein to occur and form bound immunocomplexes, c) separating the bound immunocomplexes from unbound reagents, and d) detecting the presence of the bound complexes by means of an effective label, wherein said antigenic protein of step a) comprises protein selected from-the group consisting of said antigenic protein of claim 1, said antigenic protein of claim 2 and a composition comprising a mixture of said antigenic protein of claim 1 and said antigenic protein of claim 2.

6. A method of detecting antibodies to Neospora and diagnosing neosporosis, said method comprising a) combining a sample suspected of containing said antibodies with antigenic protein which specifically detects said antibodies to form a reaction mixture, b) allowing said mixture to incubate for a time sufficient for binding between said antibodies and said antigenic protein to occur and form bound immunocomplexes, c) separating the bound immunocomplexes from unbound reagents, d) detecting the presence of the bound complexes by means of an effective label, wherein the antigenic protein of step a) comprises said immunoreagent of claim 4.

7. The method of claim 5 or 6 wherein said label is selected from the group consisting of radioactive, enzymatic, fluorescent, luminescent or chemiluminescent.

8. The method of claim 7, wherein said method is an enzyme-linked immunosorbent assay method.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 925 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Neospora caninum (ix) FEATURE:
      (A) NAME/KEY: CDS
      (B) LOCATION: 2..613

(xi) SEQUENCE DESCRIPTION: SEQ ID NO:1:

```
G ATT CGG CAC GAG GCG GGC CTG CCG AGG CTC GCT AGC GCT GGA GAC            46
  Ile Arg His Glu Ala Gly Leu Pro Arg Leu Ala Ser Ala Gly Asp
   1               5                  10                  15

TTG GCA ACC GAA CAG CAT GAA GGG GAC ATC GGA TAT GGG GTT AGG GCA          94
Leu Ala Thr Glu Gln His Glu Gly Asp Ile Gly Tyr Gly Val Arg Ala
                20                  25                  30

TAT GCC GGC GTT TCA AAC TAT GAC GGC GAT GAC GAT GCT GCA GGA AAC         142
Tyr Ala Gly Val Ser Asn Tyr Asp Gly Asp Asp Asp Ala Ala Gly Asn
             35                  40                  45

CCT GTC GAC TCG GAT GTG ACT GAC GAT GCC ATT ACA GAT GGT GAG TGG         190
Pro Val Asp Ser Asp Val Thr Asp Asp Ala Ile Thr Asp Gly Glu Trp
         50                  55                  60

CCA CGT GTT GTA TCG GGG CAG AAG CCG CAC ACG ACT CAG AAA GGC AGC         238
Pro Arg Val Val Ser Gly Gln Lys Pro His Thr Thr Gln Lys Gly Ser
     65                  70                  75

TTG ATC AAG AAG CTG GCA GTA CCG GTG GTC GGC GCT CTT ACG TCG TAT         286
Leu Ile Lys Lys Leu Ala Val Pro Val Val Gly Ala Leu Thr Ser Tyr
 80                  85                  90                  95

CTT GTT GCT GAC AGG GTG CTG CCC GAG TTG ACT TCT GCA GAA GAA GAA         334
Leu Val Ala Asp Arg Val Leu Pro Glu Leu Thr Ser Ala Glu Glu Glu
                100                 105                 110

GGA ACA GAG TCC ATC CCC GGT AAA AAA CGT GTC AAG ACT GCC GTG GGC         382
Gly Thr Glu Ser Ile Pro Gly Lys Lys Arg Val Lys Thr Ala Val Gly
             115                 120                 125
```

```
ATA GCC GCG TTA GTT GCA GCA GCC GCA TTT GCT GGA TTG GGT CTC GCG         430
Ile Ala Ala Leu Val Ala Ala Ala Ala Phe Ala Gly Leu Gly Leu Ala
        130                 135                 140

AGA ACA TTC AGG CAT TTC GTG CCA AAA AAG TCA AAG ACG GTT GCG AGT         478
Arg Thr Phe Arg His Phe Val Pro Lys Lys Ser Lys Thr Val Ala Ser
        145                 150                 155

GAG GAC TCT GCG CTC GGA AAC AGT GAA GAG CAG TAT GTG GAA GGA ACC         526
Glu Asp Ser Ala Leu Gly Asn Ser Glu Glu Gln Tyr Val Glu Gly Thr
160                 165                 170                 175

GTG AAC GGG AGC AGT GAT CCG GAA CAG GAG CGG GCG GGT GGG CCT CTT         574
Val Asn Gly Ser Ser Asp Pro Glu Gln Glu Arg Ala Gly Gly Pro Leu
                180                 185                 190

ATC CCG GAA GGA GAC GAG CAG GAA GTA GAC ACC GAA TAGTTATGGC              620
Ile Pro Glu Gly Asp Glu Gln Glu Val Asp Thr Glu
            195                 200

AAACAGATCG TTGGCGCAGC TAACATGTGT TTAACATTTT TTTCGTGTCC CAGATGACAG       680

CTGCTACTGT TTGTGTATTG TTGACAGTCC ACAGATGCGT ACGTGCCGCT CCCGTGTAGA       740

GGAAACTTTT TCTTTTTCGC CTACCTGGCC GATGAGTTCC GGGATGTGCA GTTTGTCATA       800

GGGAGCTACC CCCCTCCAAA TGGAGTTCTG CGAACCCCGT GCATGTGCTT GCGGATTTAT       860

GCTAATTGAC AGACTCGTTT CTCGATCACG AAAATCCGTA ATTTGAGAAA AAAAAAAAA        920

AAAAA                                                                   925

(2) INFORMATION FOR SEQ ID NO:2:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO:2:

Ile Arg His Glu Ala Gly Leu Pro Arg Leu Ala Ser Ala Gly Asp Leu
 1               5                  10                  15

Ala Thr Glu Gln His Glu Gly Asp Ile Gly Tyr Gly Val Arg Ala Tyr
            20                  25                  30

Ala Gly Val Ser Asn Tyr Asp Gly Asp Asp Ala Ala Gly Asn Pro
        35                  40                  45

Val Asp Ser Asp Val Thr Asp Asp Ala Ile Thr Asp Gly Glu Trp Pro
    50                  55                  60

Arg Val Val Ser Gly Gln Lys Pro His Thr Thr Gln Lys Gly Ser Leu
65                  70                  75                  80

Ile Lys Lys Leu Ala Val Pro Val Val Gly Ala Leu Thr Ser Tyr Leu
                85                  90                  95

Val Ala Asp Arg Val Leu Pro Glu Leu Thr Ser Ala Glu Glu Gly
            100                 105                 110

Thr Glu Ser Ile Pro Gly Lys Lys Arg Val Lys Thr Ala Val Gly Ile
        115                 120                 125

Ala Ala Leu Val Ala Ala Ala Phe Ala Gly Leu Gly Leu Ala Arg
    130                 135                 140

Thr Phe Arg His Phe Val Pro Lys Lys Ser Lys Thr Val Ala Ser Glu
145                 150                 155                 160

Asp Ser Ala Leu Gly Asn Ser Glu Glu Gln Tyr Val Glu Gly Thr Val
                165                 170                 175

Asn Gly Ser Ser Asp Pro Glu Gln Glu Arg Ala Gly Gly Pro Leu Ile
```

```
                    180             185              190
Pro Glu Gly Asp Glu Gln Glu Val Asp Thr Glu
            195                 200
```

(2) INFORMATION FOR SEQ ID NO:3:

(i) SEQUENCE CHARACTERISTICS:
        (A) LENGTH: 605 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Neospora caninum (ix) FEATURE:
        (A) NAME/KEY: CDS
        (B) LOCATION: 2..382

(xi) SEQUENCE DESCRIPTION: SEQ ID NO:3:

```
G AAT TCG GCA CGA GAG TAT GTC AAC TCT TCC GAG TTA GCA GGC AGT          46
  Asn Ser Ala Arg Glu Tyr Val Asn Ser Ser Glu Leu Ala Gly Ser
   1               5                  10                  15

CGT GAC AAG GGG AAC GCG GAA GCG GAA GAA GAA GCC GCT GAG GTT GAG        94
Arg Asp Lys Gly Asn Ala Glu Ala Glu Glu Glu Ala Ala Glu Val Glu
                20                  25                  30

ACT GAT GTT CAG CCT TCC AGC GTG ACG ATT GAT ACG GAG GAA CGC GCG       142
Thr Asp Val Gln Pro Ser Ser Val Thr Ile Asp Thr Glu Glu Arg Ala
            35                  40                  45

GCA CCC AGT CAG GTA CAG GTA CAG CAA GAG AGA ATG GAA GAA GCT GAC       190
Ala Pro Ser Gln Val Gln Val Gln Gln Glu Arg Met Glu Glu Ala Asp
        50                  55                  60

GAT GCT CCG AAA CCT GTT CCG GTG CGG TCG GCG GTC CCG TCT ACA GTG       238
Asp Ala Pro Lys Pro Val Pro Val Arg Ser Ala Val Pro Ser Thr Val
    65                  70                  75

GCG AAA CGG CAG CAG GCA CGT CAC AGA GTC ATT GGG ACA GCG GTG ATA       286
Ala Lys Arg Gln Gln Ala Arg His Arg Val Ile Gly Thr Ala Val Ile
 80                  85                  90                  95

GCG GCA GTA GTT GCG GCA CTT CTT TGG AAG TTT TCG AGA CGC CGA TCG       334
Ala Ala Val Val Ala Ala Leu Leu Trp Lys Phe Ser Arg Arg Arg Ser
                100                 105                 110

GGA GCT CCA CGT GAG GGG GGG GAA AAT GAA AAC GGC GGG GAG GAA AAA       382
Gly Ala Pro Arg Glu Gly Gly Glu Asn Glu Asn Gly Gly Glu Glu Lys
            115                 120                 125

TAGGAACGCC GGGGGACCAA ATGGAAACGG CGCGGGGTCA ACTGACCAAT ATGCGTATTG     442

AACAAACAGA TACACCCGGA GTGTGTAGGT GCGAGTCGCG GGGAACTCTG TGACAGTCGG     502

CGCCGAGAAA TGGCTGCGAC ACAGCCAGAC CGTCACAAGC GGGGAGGAAC GGCAAAGTTT     562

GGAGAATGCA CTTGTGGGAG AGTCGGTGGC GAGACAGCTC GAG                      605
```

(2) INFORMATION FOR SEQ ID NO:4:

(i) SEQUENCE CHARACTERISTICS:
        (A) LENGTH: 127 amino acids
        (B) TYPE: amino acid
        (D) TOPOLOGY: linear (ii) MOLECULE TYPE: protein -continued (xi) SEQUENCE DESCRIPTION: SEQ ID NO:4:

```
Asn Ser Ala Arg Glu Tyr Val Asn Ser Ser Glu Leu Ala Gly Ser Arg
 1               5                  10                  15

Asp Lys Gly Asn Ala Glu Ala Glu Glu Ala Ala Glu Val Glu Thr
            20                  25                  30

Asp Val Gln Pro Ser Ser Val Thr Ile Asp Thr Glu Glu Arg Ala Ala
            35                  40                  45

Pro Ser Gln Val Gln Val Gln Gln Glu Arg Met Glu Glu Ala Asp Asp
        50                  55                  60

Ala Pro Lys Pro Val Pro Val Arg Ser Ala Val Pro Ser Thr Val Ala
 65                  70                  75                  80

Lys Arg Gln Gln Ala Arg His Arg Val Ile Gly Thr Ala Val Ile Ala
                85                  90                  95

Ala Val Val Ala Ala Leu Leu Trp Lys Phe Ser Arg Arg Arg Ser Gly
            100                 105                 110

Ala Pro Arg Glu Gly Gly Glu Asn Glu Asn Gly Gly Glu Glu Lys
            115                 120                 125
```